United States Patent [19]

Fischer

[11] Patent Number: 5,795,776
[45] Date of Patent: Aug. 18, 1998

[54] EXPRESSION PLASMIDS REGULATED BY AN OSMB PROMOTER

[75] Inventor: Meir Fischer, Rehovot, Israel

[73] Assignee: Bio-Technology General Corp., Iselin, N.J.

[21] Appl. No.: 216,851

[22] Filed: Mar. 22, 1994

[51] Int. Cl.$^6$ .......................... C12N 15/70; C12N 15/63; C12P 21/02; C07H 21/04
[52] U.S. Cl. .................... 435/320.1; 435/69.1; 435/69.3; 435/69.4; 435/192; 435/252.33; 536/24.1
[58] Field of Search .......................... 435/69.1, 69.3, 435/69.4, 192, 197, 252.33, 320.1; 536/24.1

[56] References Cited

U.S. PATENT DOCUMENTS

| | | | |
|---|---|---|---|
| 4,624,926 | 11/1986 | Inouye et al. | 435/252.33 |
| 4,643,969 | 2/1987 | Inouye et al. | 435/69.1 |
| 4,666,836 | 5/1987 | Inouye et al. | 435/69.1 |
| 4,745,069 | 5/1988 | Mayne et al. | 435/320.1 |
| 4,757,013 | 7/1988 | Inouye et al. | 435/172.3 |
| 4,863,855 | 9/1989 | Inouye et al. | 435/69.1 |
| 4,987,070 | 1/1991 | Magota et al. | 435/69.7 |
| 5,063,158 | 11/1991 | Schoner et al. | 435/252.3 |
| 5,348,867 | 9/1994 | Georgiou et al. | 435/69.7 |

FOREIGN PATENT DOCUMENTS

| | | |
|---|---|---|
| 0055942 | 6/1988 | European Pat. Off. . |
| 0095361 | 7/1989 | European Pat. Off. . |
| 0126338 | 1/1991 | European Pat. Off. . |
| 0236330 | 6/1993 | European Pat. Off. . |

OTHER PUBLICATIONS

Jung et al., Journal of Bacteriology, 171(1), pp. 511–520 (1989) (Exhibit 14).
Jung et al., Journal of Biological Chemistry, 265(18), pp. 10574–10581 (1990) (Exhibit 15).
Ausubel et al (1992), Short Protocols in Molecular Biology, Second ed. (John Wiley & Sons, New York), pp. 1–12.
Valentin–Hansen et al. (1982), EMBO J. 1:317–322.
Fischer et al. (1990), Appl. Microbiol. Biotechnol. 33: 424–428.
Ausubel et al. (1992), Short Protocols in Molecular Biology, Second ed. (John Wiley & Sons, New York), pp. 16–1 to 16–3.
Soreq et al. (1990), Proc. Natl. Acad. Sci USA, 87: 9688–9692.
Goeddel (1979), Nature 281: 544–548.
Chang et al. (1987), EMBO J. 6(3): 675–680.

*Primary Examiner*—Nancy Degen
*Attorney, Agent, or Firm*—John P. White

[57] ABSTRACT

Plasmids are provided which upon introduction into a suitable host render the host capable of effecting expression of DNA encoding a desired polypeptide under the control of an osmB promoter. Such plasmids may be used to produce polypeptides such as superoxide dismutases, acetylcholinesterase, growth hormones and hepatitis antigen.

23 Claims, 10 Drawing Sheets

FIGURE 1

```
SEQ. ID NO. 7                           P1
                                       ↓↓↓↓
CATCCGCTCTAAGATGATTCCTGGTTGATAATTAAGACTATTTACCTGTTATTAACACTC
                 105                                       135

TCAAGATATAAAATTATTATCAGCGATATAACAGGAAGTCATTATCACCTGCGTGATATA
                 165                                       195

XmnI
                          |                              -10
ACCCTGCGCGCGAGCAGATTTCACGGAATAATTTCACCAGACTTATTCTTAGCTATTATA
                 225                                       255

P2
   ↓↓↓↓
GTTATAGAGAGCTTACTTCCGTGAATCATAAATTCAGGAGAGAGTATTATGTTTGTAACG
                 285                                       315
```

FIGURE 2

```
                    XmnI                                    ++
5'  GATCTTTTCACGGAATAATTTCACCAGACTTATTCTTAGCTATTATAGTTATAG        SEQ. ID NO. 8
    209                                               262    A

3'       AAAAGTGCCTTATTAAGTGGTCTGAATAAGAATCGATAATAT             B
              xxxxxxx                                        SEQ. ID NO. 9

++                    . RBS. :::::
5'  AGAGCTTACTTCCGTGAATCATAACTTAAGGAAATAAACA                    SEQ. ID NO. 10
    263                                  302    C

3'  CAATATCTCTCGAAGTAAGGCACTTAGTATTGAATTCCTTTATTTGTAT         D
                                        AflII              SEQ. ID NO. 11
```

```
++++       =  P2
xxxxxxx    =  sequence required for osmotic response.
...        =  base substitutions.
RBS        =  ribosomal binding site
```

FIGURE 3
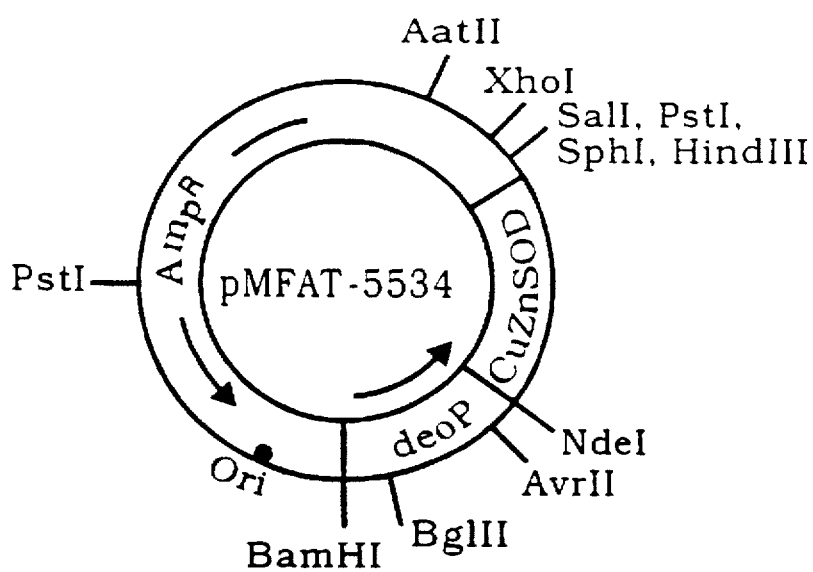
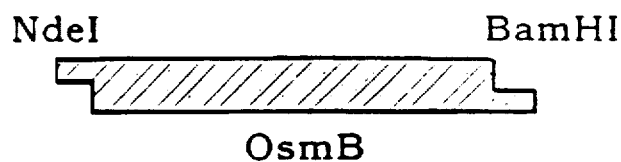
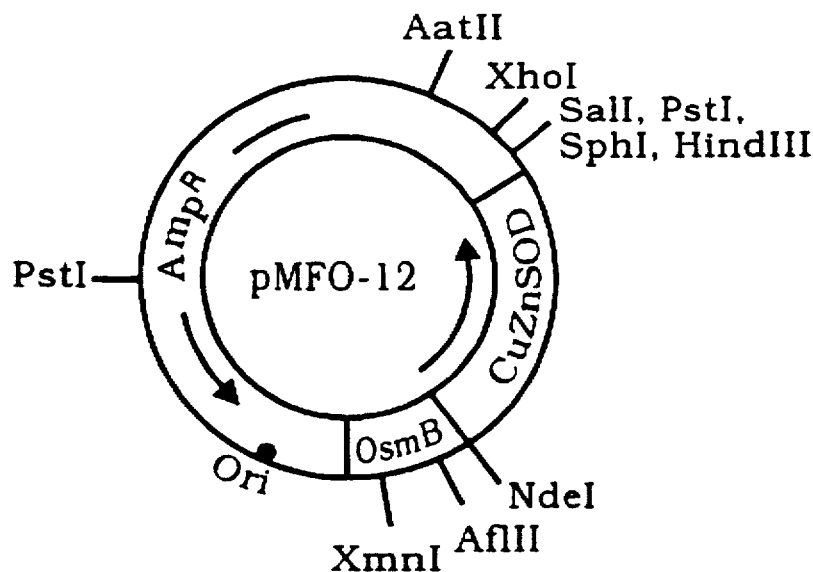

FIGURE 5
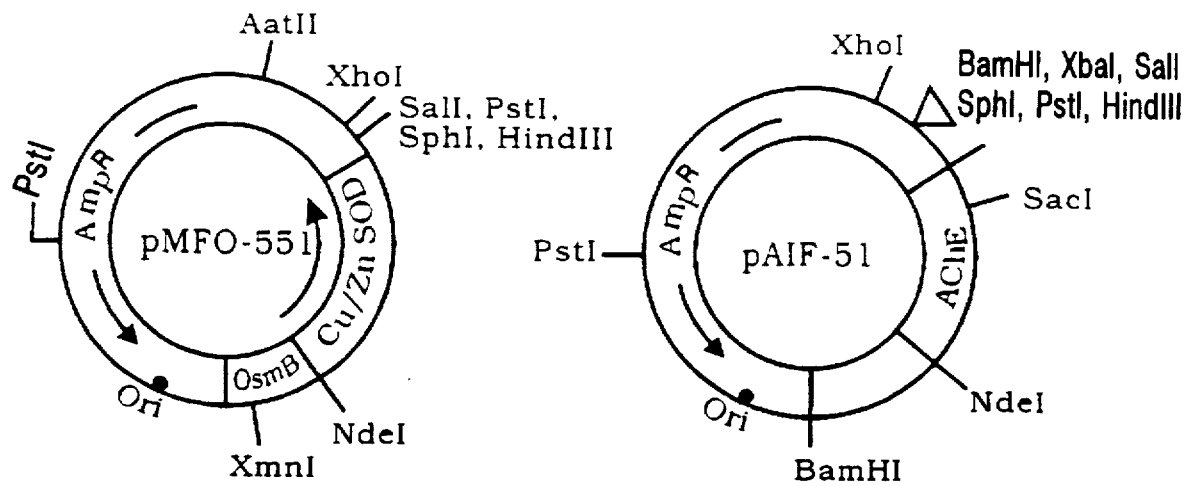
1. Cleave NdeI + HindIII
2. Isolate large fragment
1. Cleave NdeI + HindIII
2. Isolate 1900bp fragment
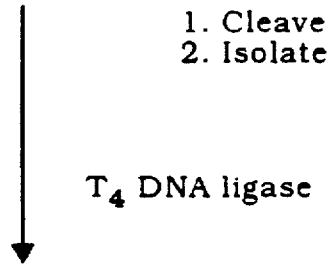
T₄ DNA ligase
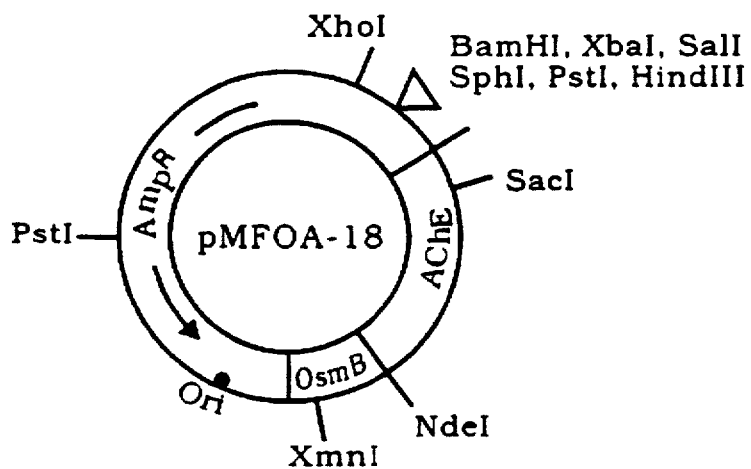

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GGCTCCAAGA GGGCCATATG TTCCCAACAT TCCC 34

( 2 ) INFORMATION FOR SEQ ID NO:2:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TATGGAACTT TCTTGGACAG TTCCTC 26

( 2 ) INFORMATION FOR SEQ ID NO:3:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TCGAGAGGAA CTGTCCAAGA AAGTTCCA 28

( 2 ) INFORMATION FOR SEQ ID NO:4:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AATTAAGATC TG                                                                                            12

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GATCCAGATC TT                                                                                            12

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGCTCCAAGA GGGCCATATG TTCCCAACAT TCCC                                                                    34

( 2 ) INFORMATION FOR SEQ ID NO:7:

( i ) SEQUENCE CHARACTERISTICS:
        ( A ) LENGTH: 240 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CATCCGCTCT AAGATGATTC CTGGTTGATA ATTAAGACTA TTTACCTGTT ATTAACACTC           60

TCAAGATATA AAATTATTAT CAGCGATATA ACAGGAAGTC ATTATCACCT GCGTGATATA          120

ACCCTGCGCG CGAGCAGATT TCACGGAATA ATTTCACCAG ACTTATTCTT AGCTATTATA          180

GTTATAGAGA GCTTACTTCC GTGAATCATA AATTCAGGAG AGAGTATTAT GTTTGTAACG          240

( 2 ) INFORMATION FOR SEQ ID NO:8:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GATCTTTTCA CGGAATAATT TCACCAGACT TATTCTTAGC TATTATAGTT ATAG  54

( 2 ) INFORMATION FOR SEQ ID NO:9:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TATAATAGCT AAGAATAAGT CTGGTGAAAT TATTCCGTGA AAA  43

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

AGAGCTTACT TCCGTGAATC ATAACTTAAG GAAATAAACA  40

( 2 ) INFORMATION FOR SEQ ID NO:11:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TATGTTTATT TCCTTAAGTT ATGATTCACG GAATGAAGCT CTCTATAAC  49

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

GGCTTCNNNN ATTCCC  16

( 2 ) INFORMATION FOR SEQ ID NO:13:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

TATGNNNNNC CTC  13

( 2 ) INFORMATION FOR SEQ ID NO:14:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TCGAGAGGNN NNNCA  15

( 2 ) INFORMATION FOR SEQ ID NO:15:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

AATTAAGATC TG  12

( 2 ) INFORMATION FOR SEQ ID NO:16:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

GGATCCAGAT CTT  13

1

EXPRESSION PLASMIDS REGULATED BY AN OSMB PROMOTER

BACKGROUND OF THE INVENTION

Throughout this specification, various publications are referenced by Arabic numerals within parentheses. Full citations for these references may be found at the end of the specification immediately preceding the claims. The disclosures of these publications in their entireties are hereby incorporated by reference into this specification in order to more fully describe the state of the art to which this invention pertains.

This application is directed towards novel expression plasmids for expression of proteins under control of an *E. coli* osmB promoter.

A number of *E. coli* promoters are known and have been applied to obtain bacterial expression of proteins. Commonly used promoters are the λ bacteriophage promoters λP$_L$ or λP$_R$ which are regulated by the thermolabile repressor cI$^{857}$. Although highly efficient in driving expression of cloned genes, the system requires the presence, in the host or in the plasmid, of the thermolabile repressor cI$^{857}$. Such systems are induced by incubating the cell culture at 42° C. The elevated temperature of induction may enhance protein misfolding and may lead to the formation of insoluble protein aggregates in the form of inclusion bodies.

Other promoters such as the tac, lac or trp promoters require induction by addition of expensive chemical inducers to the medium. With the exception of the tac expression system, most of the other promoters are weaker and less efficient than λP$_L$.

Another known promoter is the *E. coli* deo promoter. This is a constitutive promoter that shows variable promotion in the absence of glucose.

The osmB gene has been described by Jung et al. (1989) (1) and Jung et al. (1990) (2). The osmB gene, located at position 28 min on the *E. coli* chromosome, encodes an outer membrane lipoprotein containing 49 amino acids. A signal peptide directing the protein to the outer membrane is composed of 23 amino acids. The signal peptide and the osmB mature gene product are similar in many respects to the lpp gene product of *E. coli* (1). Expression of these peptides is promoted by both osmotic pressure (hyperosmolarity) and the ageing process, i.e. by entering the stationary phase of growth. Both events control expression at the level of transcription. Two transcription initiation sites have been identified by RNase protection of in-vivo message. The two initiation sites are designated P1 and P2. The site P2 is located 150 base pairs downstream from P1 and is the primary site of regulation that responds to either elevated osmolarity or to growth phase signal. The P1 promoter is activated only when both osmotic and growth phase signals are present simultaneously. A 7 base pair sequence upstream from P2 has been identified as the cis-acting regulatory element essential for the osmotic stimulation of osmB expression. Expression of osmB at the stationary phase is triggered directly from P2 (2). The nucleotide sequence of the promoter region of osmB is presented in FIG. 1 as described by Jung et al. (1).

Applicant has succeeded in producing recombinant plasmids which contain the osmB promoter. These plasmids are novel expression systems, not previously disclosed, and they can be used to produce high levels of a wide variety of recombinant polypeptides under control of the osmB promoter.

SUMMARY OF THE INVENTION

This invention provides a method for producing a recombinant polypeptide by use of a plasmid comprising an osmB promoter derived from *E. coli* and DNA encoding the recombinant polypeptide which comprises culturing a microorganism transformed by the plasmid under conditions permitting expression of the recombinant polypeptide and recovering the recombinant polypeptide so produced.

This invention further provides a plasmid which upon introduction into a suitable host cell renders the host capable of effecting expression of DNA encoding a desired polypeptide, and thereby effecting production of the polypeptide comprising in 5' to 3' order DNA which includes an *E. coli* osmB promoter, DNA which includes a ribosomal binding site for rendering mRNA transcribed from the DNA encoding the polypeptide capable of binding to ribosomes within the host cell, an ATG initiation codon, DNA encoding the polypeptide in phase with the ATG initiation codon, a DNA sequence comprising an origin of replication from a bacterial plasmid capable of autonomous replication in the host cell and a DNA sequence which contains a gene associated with a selectable or identifiable trait which is manifested when the plasmid is present in the host cell.

BRIEF DESCRIPTION OF THE FIGURES

The restriction maps for each of the plasmids shown in FIGS. 3–10 do not identify all the restriction sites present on each plasmid. In some cases restriction sites are shown in one figure, but not in another. However, in all cases those restriction sites necessary to enable one skilled in the art to practice the invention are shown. The relative sizes of the various plasmids are not drawn to scale and no conclusions may be drawn concerning the size of the plasmids or any inserts, from the figures.

FIG. 1: Nucleotide Sequence of the Promoter Region of osmB

The nucleotide sequence (SEQ. ID NO. 7) of the promoter region of osmB as described by Jung et al. (1) is depicted. The notations "P1" and "P2" refer to the transcription initiation sites.

FIG. 2: Modified Synthetic Nucleotide Sequence of the Promoter Region of osmB

A synthetic osmB sequence is depicted (SEQ. ID NOS. 8–11). This sequence contains the osmB P2 promoter and osmB ribosomal binding site (modified) and has inter alia the following restriction enzyme sites: XmnI (nucleotides 221–225) and AflII (nucleotides 287–292).

The numbering of the nucleotides in FIG. 2 corresponds to the numbering in Jung, et al.(1).

FIG. 3: Construction of Plasmid pMFO-12

Plasmid pMFO-12 was constructed by ligating a large fragment containing the coding region for copper-zinc superoxide dismutase (CuZnSOD), obtained by BamHI and NdeI digestion of plasmid pMFAT-5534, with the synthetic sequence encoding the modified osmB promoter region as described in FIG. 2 and Example 1.

Plasmid pMFAT-5534 is very similar to plasmid pMF-5534 (ATCC Accession No. 67703). Plasmid pMFAT-5534 contains the deo promoter in the opposite orientation in comparison to plasmid pMF-5534. Digestion of plasmid pMF-5534 with BamHI followed by religation will produce the two orientations in a 1:1 ratio. In addition, plasmid pMFAT-5534 has a TrpA transcription termination sequence flanked by XhoI, which plasmid pMF-5534 lacks (Wu et al., PNAS 75: 5442–5446 (1978)).

Figure 4:
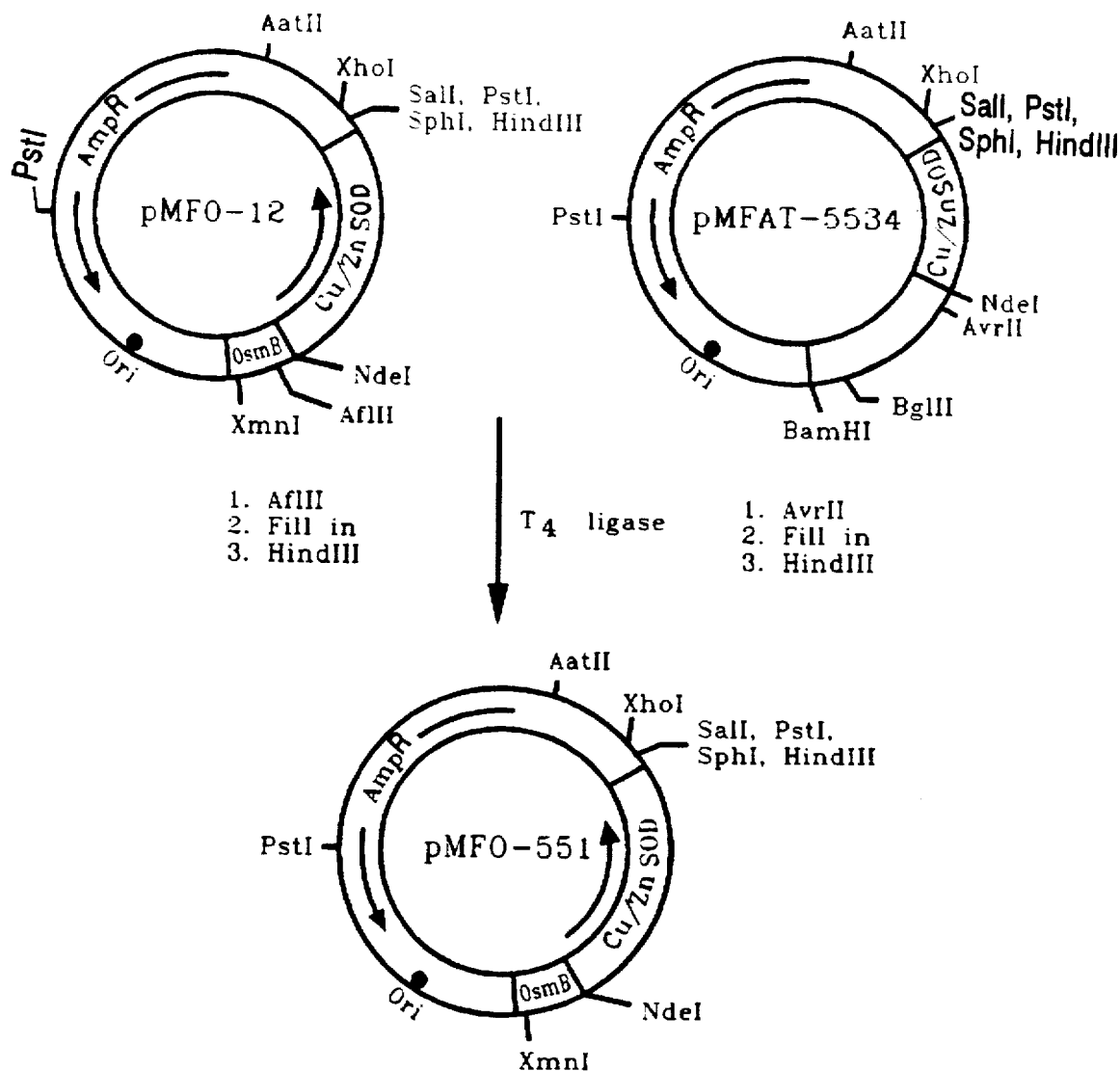

FIG. 4: Construction of Plasmid pMFO-551

Plasmid pMFAT-5534 was cleaved with AvrII and the 5' end filled in by treatment with *E. coli* DNA polymerase (Klenow fragment). The linear pMFAT-5534 was then cleaved with HindIII. A 600 bp fragment containing the deo ribosomal binding site and the coding region for CuZnSOD was obtained.

Plasmid pMFO-551 (ATCC Accession No. 69339) was constructed by ligating the 600 bp fragment obtained from plasmid pMFAT-5534 as described above with the large fragment of plasmid pMFO-12 obtained by cleavage with AflIII, fill in of the 5' end with E. coli DNA polymerase, and then cleavage with HindIII. In the resulting plasmid pMFO-551, the deo ribosomal binding site is present just upstream of the NdeI site.

FIG. 5: Construction of Plasmid pMFOA-18

Plasmid pMFOA-18 (ATCC Accession No. 69340) was constructed by ligating a 1900 bp fragment containing the coding region for acetylcholinesterase (AChE), obtained by NdeI and HindIII digestion of pAIF-51 with the large fragment of NdeI and HindIII digested pMFO-551.

The AChE fragment could similarly have been obtained from plasmid pAIF-34 (ATCC Accession No. 68638) since both plasmids pAIF-51 and pAIF-34 contain the same AChE fragment (6, 7).

Figure 6:
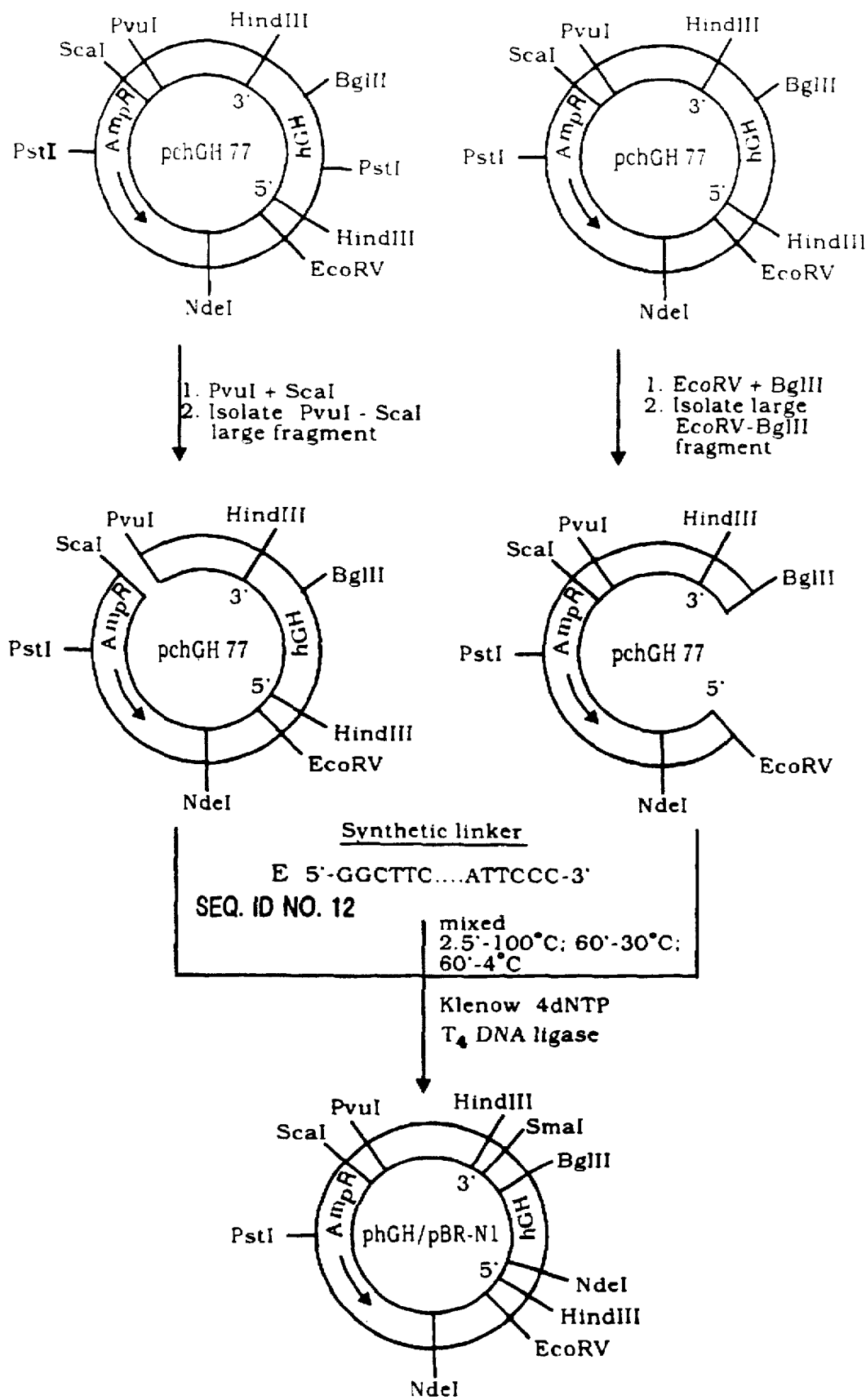

FIG. 6: Construction of Plasmid phGH/PBR-N1

Plasmid phGH/pBR-N1 was constructed by tripartite ligation of the large fragment of PvuI and ScaI digested plasmid pchGH77 (ATCC Accession No. 69359) with the large fragment of EcoRV and BglII digested pchGH77 and with the following synthetic oligomer (SEQ. ID NO. 1):

E 5'-GGCTCCAAGAGGGCCATATGTTCCCAACATTCCC-3'
                      NdeI

Figure 7:
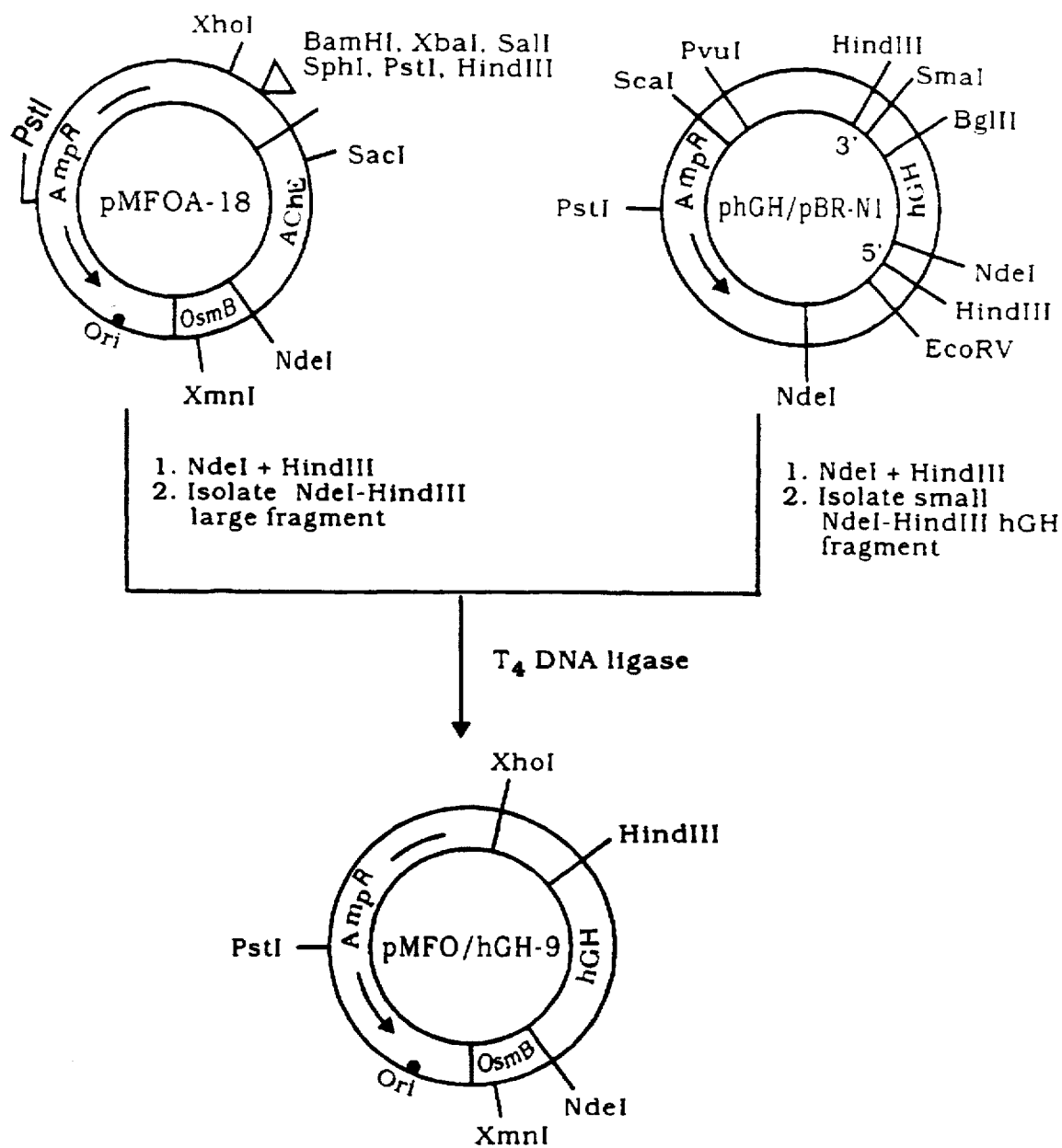

FIG. 7: Construction of Plasmid pMFO/hGH-9

Plasmid pMFO/hGH-9 (ATCC Accession No. 69360) was constructed by ligating the large fragment of NdeI and HindIII digested plasmid pMFOA-18 (which carries the osmB promoter) with the small fragment of NdeI and HindIII digested plasmid phGH/pBR-N1.

Figure 8:
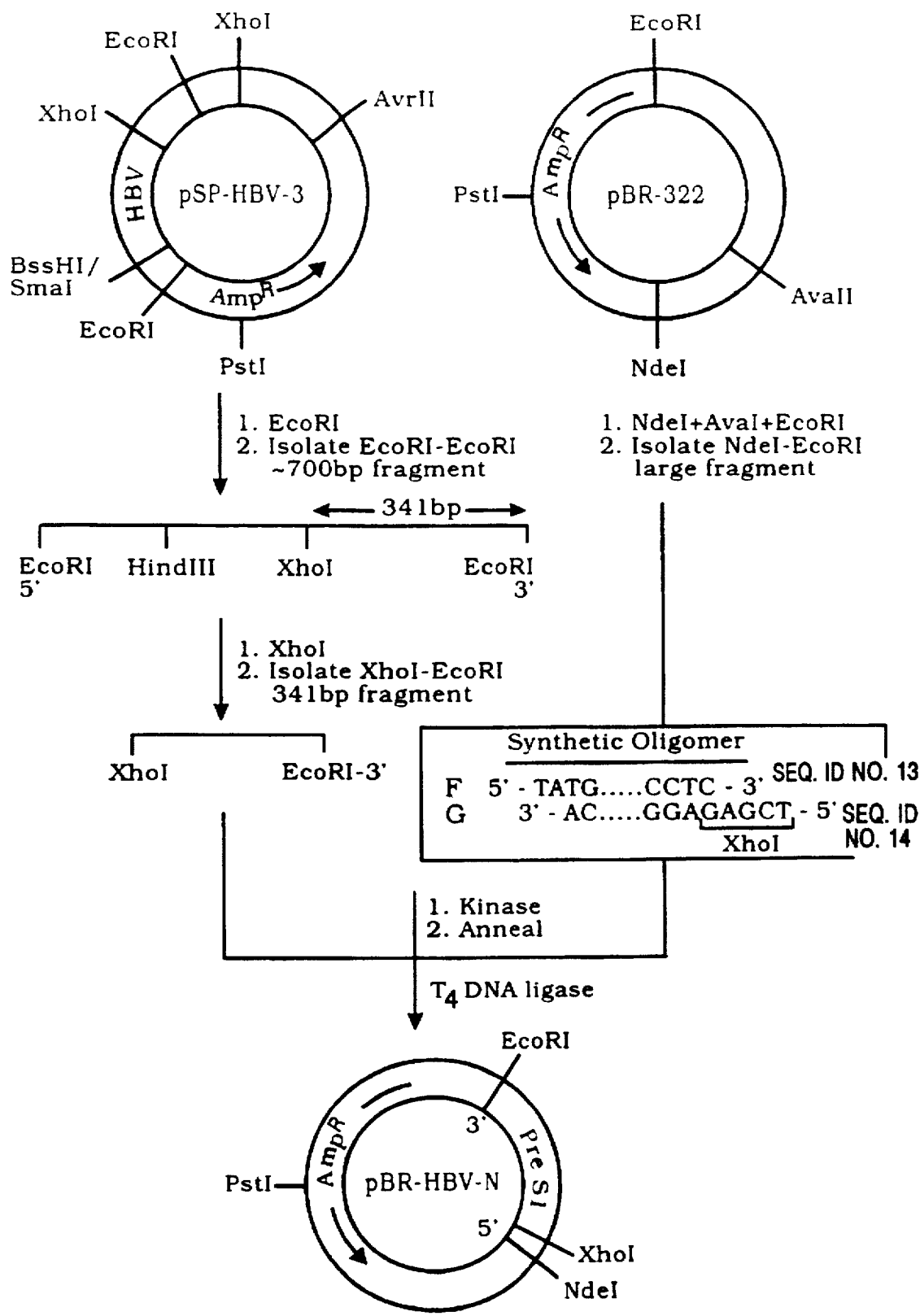

FIG. 8: Construction of Plasmid pBR-HBV-N

Plasmid pSP-HBV-3 was digested with EcoRI and the EcoRI-EcoRI 700 bp fragment was isolated and cleaved with XhoI. The XhoI-EcoRI 341 bp fragment encoding HBV-PreS1, was isolated.

Plasmid pBR-HBV-N was constructed by tripartite ligation of the XhoI-EcoRI 341 bp fragment obtained as described above with the large fragment of NdeI, AvaI and EcoRI digested pBR-322 (ATCC Accession No. 37017) and with the following synthetic oligomers (SEQ. ID NOS. 2 & 3):

initiation

F 5'-TATGGAACTTTCTTGGACAGTTCCTC    -3'

Figure 9:
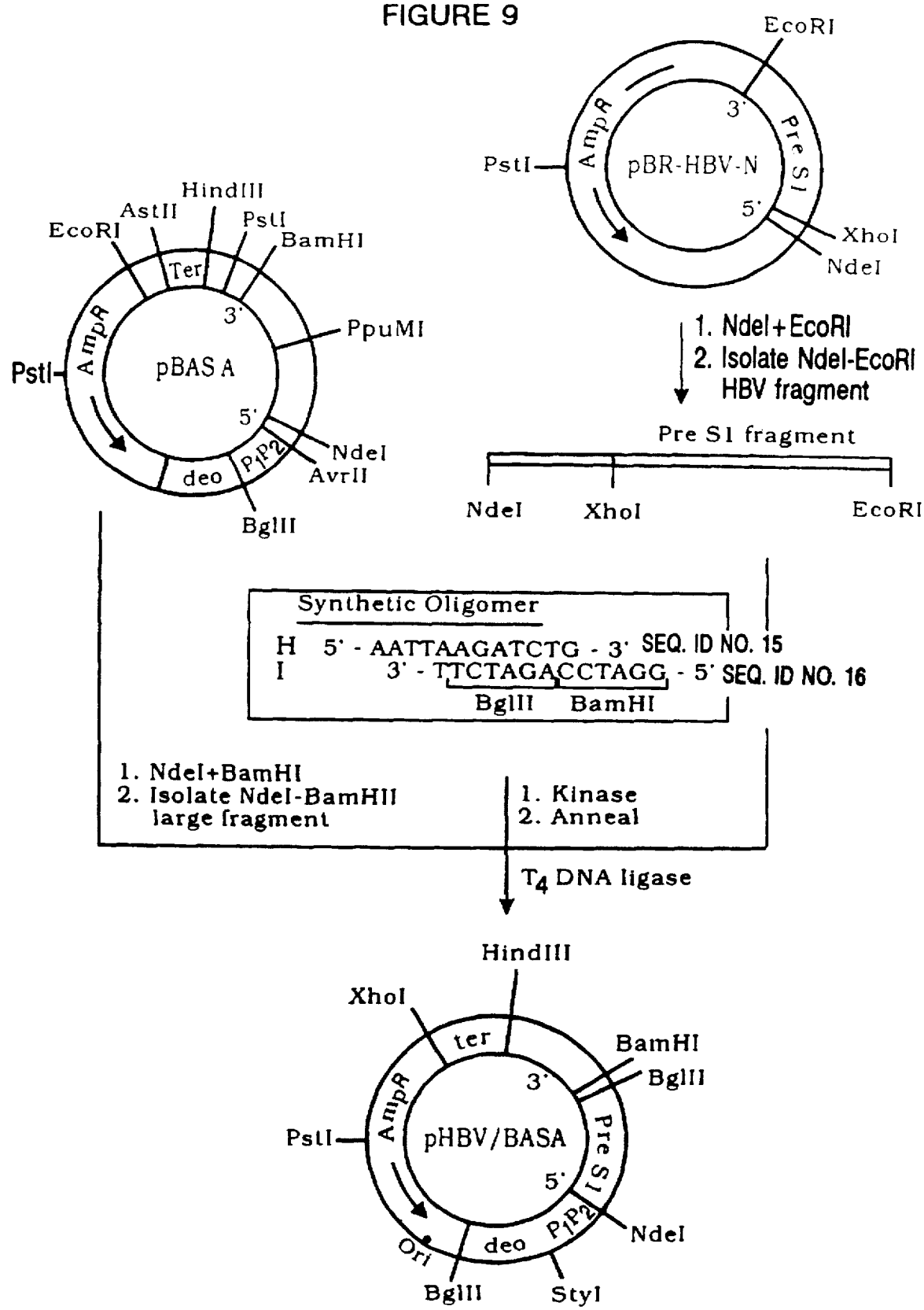

G 3'-___ACCTTGAAAGAACCTGTCAAGGAGAGCT-5'
     NdeI                              XhoI
     complementary site FIG. 9: Construction of Plasmid pHBV/BASA Plasmid pHBV/BASA was constructed by tripartite ligation of the large fragment of NdeI and BamHI digested plasmid pBASA with the PreS1 fragment of plasmid pBR-HBV-N digested with NdeI and EcoRI and with the following synthetic oligomers (SEQ. ID NOS. 4 & 5):

H 5'-AATTAAGATCTG         -3'

I 3'-        TTCTAGACCTAG-5'
             BglII  BamHI

Figure 10:
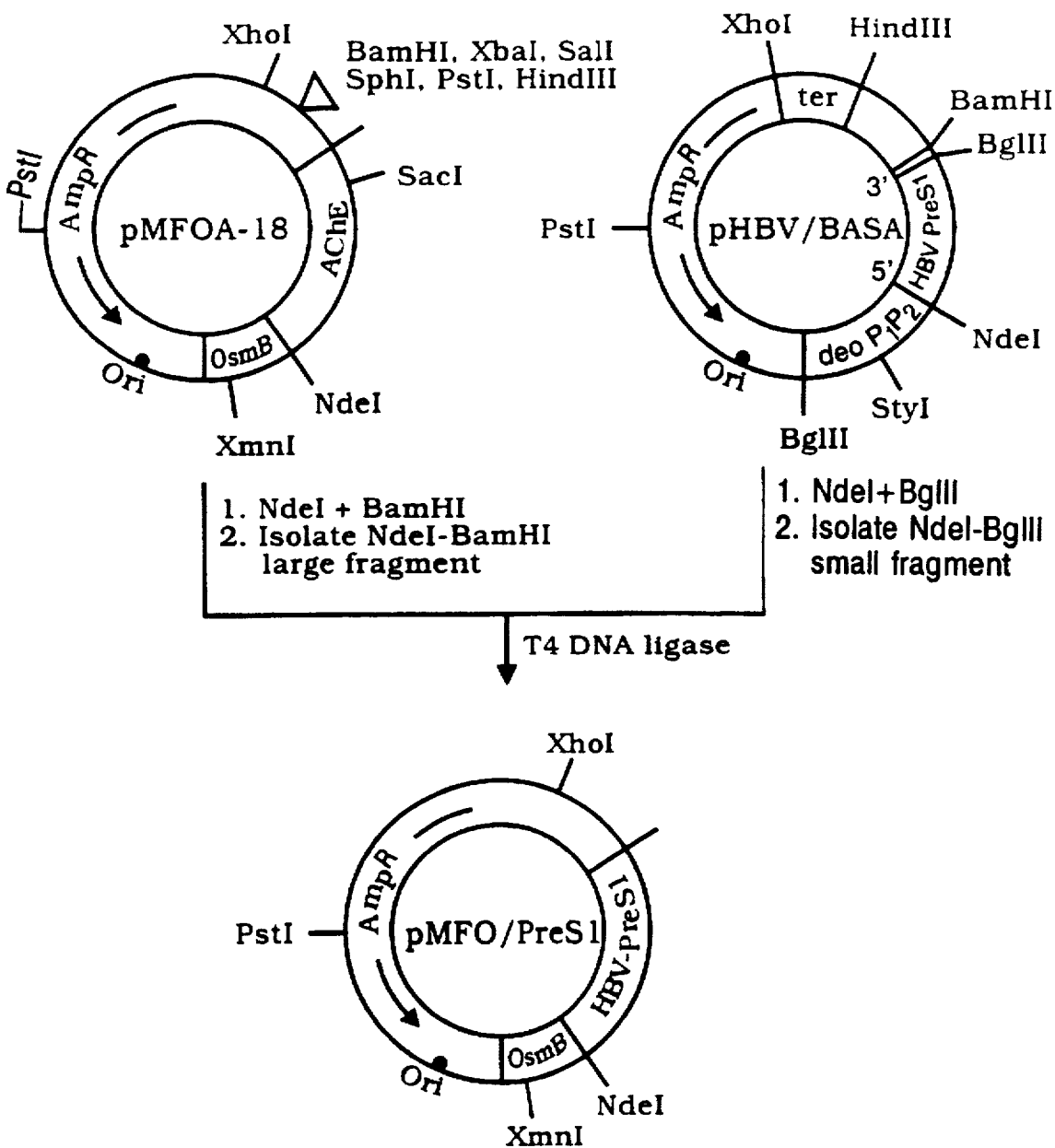

FIG. 10: Construction of Plasmid pMFO/PreS1

Plasmid pMFO-PreS1 (ATCC Accession No. 69358) was constructed by ligating the large fragment of NdeI and BamHI digested plasmid pMFOA-18 (which encodes the osmB promoter) with the small fragment of NdeI and BglII digested plasmid pHBV/BASA.

DETAILED DESCRIPTION OF THE INVENTION

The plasmids pMFO-551 and pMFOA-18 were deposited in E. coli pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 69339 and 69340 respectively on Jun. 29, 1993.

The plasmids pchGH77, pMFO/hGH-9 and pMFO/PreS1 were deposited in E. coli pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 69359, 69360 and 69358, respectively on Jul. 26, 1993.

The invention provides novel expression plasmids for expression of polypeptides (proteins) under the control of an osmB promoter.

The term "E. coli osmB promoter" as used herein encompasses any naturally-occurring osmB promoter, modified osmB promoter, synthetic osmB promoter and synthetic derivatives of the osmB promoter provided that such modified or synthetic derivatives have the promoter activity of the naturally-occurring osmB promoter from E. coli.

Synthetic derivatives of the osmB promoter and/or modified osmB promoter as used herein encompass a DNA sequence similar to the naturally-occurring DNA sequence encoding the E. coli osmB promoter, to which one or more nucleotides have been added to either the 3' end, the 5' end or both, and/or to which substitutions and/or deletions to the sequence have been made, and which has the promoting activity of the naturally-occurring osmB promoter.

The plasmids of the subject invention may express and produce procaryotic and eucaryotic polypeptides (proteins).

Examples of polypeptides (proteins) which may be expressed and produced by the plasmids of the subject invention are mammalian pituitary hormones such as growth hormones, prolactins and other pituitary hormones, enzymes such as superoxide dismutase and acetylcholinesterase (AChE), antigens such as hepatitis antigens, and others.

The term "polypeptide" as used herein encompasses homologs of the naturally occurring polypeptide.

As used herein, the term "homolog" of a polypeptide is a polypeptide which has substantially the same amino acid sequence and substantially the same biological activity as the naturally-occurring polypeptide. Thus, a homolog may differ from the naturally-occurring polypeptide by the addition, deletion, or substitution of one or more non-essential amino acid residues, provided that the resulting polypeptide retains the biological activity of the naturally-occurring polypeptide. Persons skilled in the art can readily determine which amino acids residues may be added, deleted, or substituted (including with which amino acids such substitutions may be made) using established well known procedures, including, for example, conventional methods for the design and manufacture of DNA sequences coding for bacterial expression of polypeptide homologs, the modification of cDNA and genomic sequences by site-directed mutagenesis techniques, the construction of recombinant polypeptides and expression vectors, the bacterial expression of the polypeptides, and the measurement of the biochemical activity of the polypeptides using conventional biochemical assays.

Examples of homologs expressed by the plasmids of the subject invention are deletion homologs containing less than all the residues comprising the naturally-occurring polypeptide, substitution homologs wherein one or more residues are replaced by other residues, and addition homologs wherein one or more amino acids residues are added to a terminal or medial portion of the polypeptide, all of which have the biological activity of the naturally-occurring polypeptide.

Substitutions of amino acids may be designed in accordance with the homologous or equivalence groups as described by e.g. Albert L. Lehninger, Biochemistry, Second Edition, Worth Publishers Inc. (1975), Chapter 4 or Margaret O. Dayhoff, Atlas of Protein Sequence and Structure, Volume 5, The National Biomedical Research Foundation (1972), Chapter 9.

The DNA may be mutated by methods known to those skilled in the art, e.g. Bauer et al. (1985), Gene 37: 73–81. The mutated sequence may be inserted into suitable expression vectors as described herein, which are introduced into cells which are then treated so that the mutated DNA directs expression of the polypeptide homolog.

The plasmids of the subject invention comprising a sequence encoding a polypeptide may be adapted for expression in bacterial, yeast, or mammalian cells. The plasmids must additionally comprise the regulatory elements necessary for expression of the cloned gene in the bacteria, yeast, or mammalian cells so located relative to the nucleic acid encoding the polypeptide as to permit expression thereof. Regulatory elements required for expression include osmB promotor sequences to bind RNA polymerase and a ribosomal binding site for ribosome binding.

Those skilled in the art will understand that the plasmids deposited in connection with this application may be readily altered by known techniques (e.g. by site-directed mutagenesis or by insertion of linkers) to encode and promote expression of homologs. Such techniques are described for example in Sambrook, J., Fritsch, E. F. and Maniatis, T. (1989) Molecular Cloning: A Laboratory Manual, 2nd edition, Cold Spring Harbor Laboratory Press. The plasmids may also be altered to encode and promote expression of other polypeptides.

The suitable regulatory elements are positioned within the plasmid relative to the DNA encoding the polypeptide so as to effect expression of the polypeptide in a suitable host cell. In preferred embodiments of the invention, the regulatory elements are positioned close to and upstream of the DNA encoding the polypeptide.

Various ribosomal binding sites (RBS's), for rendering mRNA transcribed from DNA encoding a desired polypeptide, capable of binding to ribosomes within the host cell, are also included in the subject invention, such as the osmB RBS and the deo RBS.

The plasmids of the invention also contain an ATG initiation codon. The DNA encoding the desired polypeptide is in phase with the ATG initiation codon.

The plasmids of the invention also include a DNA sequence comprising an origin of replication from a bacterial plasmid capable of autonomous replication in the host cell. Suitable origins of replication may be obtained from numerous sources, such as from plasmid pBR322 (ATCC Accession No. 37017).

The plasmids of the subject invention also include a DNA sequence which contains a gene associated with a selectable or identifiable phenotypic trait which is manifested when the plasmid is present in the host cell such as a drug resistance gene, e.g. resistance to ampicillin, chloramphenicol or tetracycline.

Preferred bacterial host cells are $E.\ coli$ cells. Examples of suitable $E.\ coli$ cells are strains S$\phi$930 (ATCC Accession No. 67706) or W2637 ($E.\ coli$ Genetic Stock Center, Yale University, New Haven, Conn.) or S$\phi$732 (ATCC Accession No. 67362) or MC1655 (ATCC Accession No. 69339) or MC1061 (ATCC Accession No. 67364) or W3110 (ATCC Accession No. 67705) or MG294 ($E.\ coli$ Genetic Stock Center, Yale University, New Haven, Conn.), but other $E.\ coli$ strains and other bacteria can also be used as hosts for the plasmids. One skilled in the art is able to determine other appropriate hosts for using the methods of this invention.

The bacteria used as hosts may be any strains including auxotrophic strains, prototrophic strains, lytic strains, $F^+$ and $F^-$ strains and other strains.

All the $E.\ coli$ host strains described can be "cured" of the plasmids they harbor by methods well known in the art, e.g. the ethidium bromide method described by R. P. Novick in *Bacteriol. Review* 33, 210 (1969).

The subject invention provides a method for producing a recombinant polypeptide by use of a plasmid comprising an osmB promoter derived from $E.\ coli$ and DNA encoding the recombinant polypeptide.

The subject invention further provides a plasmid which upon introduction into a suitable host cell renders the host capable of effecting expression of DNA encoding a desired polypeptide, and thereby effecting production of the polypeptide comprising in 5' to 3' order DNA which includes an $E.\ coli$ osmB promoter, DNA which includes a ribosomal binding site for rendering mRNA transcribed from the DNA encoding the polypeptide capable of binding to ribosomes within the host cell, an ATG initiation codon, DNA encoding the polypeptide in phase with the ATG initiation codon, a DNA sequence comprising an origin of replication from a bacterial plasmid capable of autonomous replication in the host cell and a DNA sequence which contains a gene associated with a selectable or identifiable trait which is manifested when the plasmid is present in the host cell.

In a preferred embodiment the $E.\ coli$ osmB promoter and ribosomal binding site are those depicted in FIG. 2.

In an especially preferred embodiment the ribosomal binding site is derived from the $E.\ coli$ deo operon.

In preferred embodiments the polypeptide is selected from the group consisting of human copper-zinc superoxide dismutase, acetylcholinesterase, human growth hormone and pre-S1 hepatitis antigen.

In one embodiment the host cell is a bacterial cell and in a preferred embodiment the bacterial cell is an $E.\ coli$ cell.

In an especially preferred embodiment the $E.\ coli$ cell is $E.\ coli$ MC1655 containing plasmid pMFO-551 deposited under ATCC Accession No. 69339 or $E.\ coli$ MC1061 containing plasmid pMFOA-18 deposited under ATCC Accession No. 69340 or *E. coli* MC1061 containing plasmid pMFO/hGH-9 deposited under ATCC Accession No. 69360 or *E. coli* MC1061 containing plasmid pMFO-PreS1 deposited under ATCC Accession No. 69358.

The subject invention also provides a plasmid for the production of human copper zinc superoxide dismutase designated pMFO-551 deposited under ATCC Accession No. 69339 and a plasmid for the production of human acetylcholinesterase designated pMFOA-18 deposited under ATCC Accession No. 69340 and a plasmid for the production of human growth hormone designated pMFO/hGH-9 deposited under ATCC Accession No. 69360 a plasmid for the production of PreS1 hepatitis antigen designated pMFO-PreS1 deposited under ATCC Accession No. 69358.

The subject invention further provides a host plasmid system for the production of a recombinant polypeptide comprising a plasmid of the subject invention in a suitable host cell.

In one embodiment the host cell is a bacterial host cell. In another embodiment the bacterial host cell is *E. coli*. In a preferred embodiment *E. coli* host cell is *E. coli* strain MC1655 or *E. coli* strain MC1061.

The subject invention further provides a method for producing CuZnSOD which comprises growing a host plasmid system of the subject invention under conditions permitting production of the CuZnSOD and recovering the CuZnSOD.

The subject invention also provides a method for producing AChE which comprises growing a host plasmid system of the subject invention under conditions permitting production of the AChE and recovering the AChE.

The subject invention additionally provides a method for producing hGH which comprises growing a host plasmid system of the subject invention under conditions permitting production of the hGH and recovering the hGH.

The subject invention furthermore provides a method for producing PreS1 hepatitis antigen which comprises growing a host plasmid system of the subject invention under conditions permitting production of the PreS1 hepatitis antigen and recovering the PreS1 hepatitis antigen.

In summary, applicants have produced a novel expression system, using an osmB promoter which has advantages over existing promoters as shown in Table I below. This Table provides a comparison of the advantages of the osmB promoter expression system over other promoter expression systems.

Additionally, a surprising feature of the osmB promoter system in expression plasmids is the high level of polypeptide produced under its control.

TABLE 1

| osmB Promoter | λ $P_L$ | Deo | Tac, Lac, Trp |
|---|---|---|---|
| Expression promoted by inexpensive NaCl or ageing[1]. | Thermo-inducible at 38° C.–42° C. | Variable "promotion" in the absence of glucose. | Expensive chemical inducers. |
| Growth and expression at any temperature between 28° C.–42° C. | Requires temperature manipulations for growth and expression at 30° C.–32° C. | Growth and expression at any temperature between 30° C.–42° C. | Growth and expression at 28° C.–42° C.; chemical manipulations required. |
| No need for specialized host. | Requires specialized host. | Specialized host preferable. | |
| Economical. | Less economical due to higher energy requirement. | less economical due to glycerol usage. | Not economical at all due to expensive chemical inducers. |

[1] The osmB promoter is a "promotable" constitutive promoter.

EXAMPLES

The following examples are provided to illustrate the invention, but are not intended to, and should not be construed to, in any way limit the scope of the invention as defined by the claims which follow.

The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems or determining the identity of such polypeptides by activity staining of isoelectric focusing (IEF) gels. Such methods are well known to those of ordinary skill in the art and are described in numerous publications, the disclosures of which are hereby incorporated by reference into this specification, including by way of example the following:

Sambrook, J., Fritsch, E. F. and Maniatis, T. (1989) *Molecular Cloning: A Laboratory Manual*, 2nd edition, Cold Spring Harbor Laboratory Press, New York.

J. M. McCord and I. Fridovich (1969), J. Biol. Chem. 244: 6049–55.

C. Beauchamp and I. Fridovich (1971), Anal. Biochem. 44: 276–287.

Example 1: Construction of SOD Expression Plasmid

A vector containing a promoter derived from the osmB promoter was prepared by construction, using methods known in the art, of a synthetic sequence of about 100 base pairs containing an altered 3' end relative to the naturally occurring nucleotide sequence.

The four synthetic sequences A–D shown in FIG. 2 were prepared.

Oligonucleotides B and C were phosphorylated at the 5' end by polynucleotide kinase and then mixed with the complementary strand to generate two duplexes as shown above. About 25 pmol of each of the duplexes were then mixed and ligated with T4 DNA ligase. The ligated oligonucleotides were inserted into plasmid pMFAT-5534 cleaved with NdeI-BamHI (FIG. 3). The resulting plasmid designated pMFO-12 contains the synthetic osmB sequence containing the osmB P2 promoter and ribosomal binding site fused to the human CuZnSOD gene. Plasmid pMFO-12 was introduced into *Escherichia coli* MC1061 and tested for expression of human CuZnSOD.

Total cell extract of host containing the osmB driven expression system was analyzed by SDS-polyacrylamide gel electrophoresis. The zymogram obtained revealed a protein band corresponding to the size of CuZnSOD. Expression was estimated to be about 1–2% of total cell protein.

Example 2: Improved osmB Expression Plasmid

The expression level of plasmid pMFO-12 was 1–2% of the total protein. In an attempt to improve the level of expression, the osmB ribosomal binding site was replaced with the deo ribosomal binding site by the procedure described in FIG. 4. The resulting plasmid designated pMFO-551 (FIG. 4, ATCC Accession No. 69339) containing the human CuZnSOD gene under control of the osmB promoter and deo ribosomal binding site was introduced into *E. coli* prototrophic hosts Sφ930 (ATCC Accession No. 67706), W2637 (*E. coli* Genetic Stock Center, Yale University, New Haven, Conn.), Sφ732 (ATCC Accession No. 67362) and MC1655 (ATCC Accession No. 69339).

In order to determine the influence of the host on the expression of CuZnSOD by plasmid pMFO-551, the above referenced four hosts containing plasmid pMFO-551 were grown in LB medium supplemented with 1×M9 salts and 0.1–0.2% glucose at 37° C. for 18 h. One ml of the cultures was harvested and total cell lysates were subjected to SDS-PAGE analysis.

The results of SDS-PAGE showed that expression of CuZnSOD by the osmB promoter is host dependent. In W2637 the level of CuZnSOD expression was not higher than 1% of total cell protein while the level of expression in Sφ930 and Sφ732 was about 15%. The highest level of expression of about 25% of total cell protein was obtained with MC1655.

Example 3: Comparison of Expression of CuZnSOD Under Control of osmB, deo, and λP$_L$ Promoters One advantage of the osmB promoter was determined by the observation of increased levels of expression of protein under control of the osmB promoter in comparison to the expression of protein under control of the λP$_L$ promoter and the deo promoter.

Bacterial growth was performed according to methods known in the art essentially as described by Hartman et al. (3, 5) and Fischer et al. (4).

The strains tested were:

1. *E. coli* A4255 containing plasmid pSODβ$_1$T$_{11}$ (λP$_L$ promoter, ATCC Accession No. 53468)

2. *E. coli* Sφ930 containing plasmid pMF-5534 (deo promoter, ATCC Accession No. 67703).

3. *E. coli* MC1655 containing plasmid pMFO-551 (osmB promoter, ATCC Accession No.69339).

Plasmids pMF-5534 and pMFO-551 provide constitutive expression in contrast to plasmid pSODβ$_1$T$_{11}$ which requires induction by heating to 42° C.

Host plasmid systems *E. coli* A4255 containing plasmid pSODβ$_1$T$_{11}$ and *E. coli* Sφ930 containing plasmid pMF-5534 were optimized for expression of CuZnSOD.

The base growth media contained:

| | |
|---|---|
| Tryptone | 10 g |
| Yeast extract | 5 g |
| NaCl | 5 g |
| Glucose* | 1 g |
| Deionized H$_2$O | 1 L |

*Added from sterile stock solution after autoclave.

The base medium also contains the following supplements which are necessary cofactors for obtaining enzymatic activity of the specific polypeptide produced by these three strains (CuZnSOD).

| | |
|---|---|
| CuSO$_4$.5H$_2$O | 0.48 g |
| ZnSO$_4$.7H$_2$O | 0.009 g |

The complete medium therefore contains 123 ppm Cu$^{++}$ and 2 ppm Zn$^{++}$. The appropriate antibiotic was added under sterile conditions following autoclaving.

Duplicate cultures of *E. coli* A4255 containing plasmid pSODβ$_1$T$_{11}$, under control of the lambda promoter, were cultivated in the presence of 12.5 mg/L tetracycline at 30° C. until the O.D.$_{660}$ reached 1.1. The culture was then induced by heating at 42° C. for 15 minutes followed by 75 minutes at 38° C. Cultures were sampled at the end of the induction period.

Duplicate cultures of *E. coli* strain Sφ930 containing plasmid pMF-5534 and *E. coli* strain MC1655 containing plasmid pMFO-551 were cultivated at 30° C. in the presence of 100 mg/L sodium ampicillin. Cultures were inoculated from starters, incubated overnight and sampled the following morning.

For each sample, culture optical density at 660 nm was measured and dry cell weights (DCW) were calculated using the formula 1 O.D. unit=0.38 g/L DCW.

Samples were centrifuged in a tabletop Eppendorf centrifuge (14,000 rpm) for 10 minutes and the supernatants discarded. Pellets were stored frozen until analysis.

The pellets were analyzed both by SDS-PAGE under reducing conditions and by SOD activity determination using the xanthine-xanthine oxidase method of McCord and Fridovich (J. Biol. Chem. 244:6049–6055). The specific productivity of CuZnSOD equals mg of active CuZnSOD per mg of dry cell weight (DCW).

A comparison of CuZnSOD enzyme activity obtained from these three host plasmid systems is presented in Table 2.

TABLE 2

Comparison of CuZnSOD productivity data in three E. coli Expression Systems in Rich Media.

| Culture No. | Strain | Promoter | O.D. (660 nm) | DCW (mg/L) | SOD Activity (mg/L) | Specific Productivity (mg active CuZnSOD/mg DCW) | Average Specific Productivity |
|---|---|---|---|---|---|---|---|
| 1 | A4255 | λP$_L$ | 1.94 | 737 | 16.0 | 0.022 | 0.021 |
| 2 | pSODβ$_1$T$_{11}$ | | 1.86 | 707 | 17.0 | 0.024 | |
| 3 | Sϕ930 | deo | 2.16 | 821 | 16.0 | 0.019 | 0.025 |
| 4 | pMF-5534 | | 2.00 | 760 | 23.9 | 0.031 | |
| 5 | MC1655 | OsmB | 2.49 | 946 | 78.0 | 0.082 | 0.085 |
| 6 | pMFO-551 | | 2.75 | 1045 | 91.7 | 0.088 | |

The results clearly show that the highest specific productivity of CuZnSOD in the strains tested was obtained with plasmid pMFO-551 under control of the osmB promoter and was 3-4 fold higher than the level achieved by the other two plasmids.

Example 4: Expression of CuZnSOD Under Control of the osmB Promoter in Minimal Medium In order to further investigate the properties of the osmB promoter, a further comparison of the two constitutive strains described above bearing the osmB and deo promoters respectively was performed in minimal medium.

| Glucose Mineral Salts Medium | |
|---|---|
| K$_2$HPO$_4$ | 9 g |
| KH$_2$PO$_4$ | 1 g |
| NaCl | 5 g |
| NH$_4$Cl | 1 g |
| MgSO$_4$.7H$_2$O | 0.2 g |
| FeNH$_4$ citrate | 0.01 g |
| Trace elements | 1 ml |
| Biotin | 0.5 mg |
| Yeast extract | 0.1 g |
| Glucose* | 2 g |
| Sodium ampicillin* | 0.1 g |
| Deionized water | 1 L |

*Added after autoclaving from sterile stock solution

A sterile solution containing the following is added per liter of sterile medium after autoclaving:

| | |
|---|---|
| CuSO$_4$.5H$_2$O | 0.48 g |
| Trisodium citrate | 0.69 g |
| ZnSO$_4$.7H$_2$O | 0.009 g |

This supplementation results in the medium containing 123 ppm Cu$^{++}$ and 2 ppm Zn$^{++}$.

The experiment was performed essentially as described in Example 3 and the results are provided in Table 3. In this case too, host plasmid system E. coli Sϕ930 containing plasmid pMF-5534 was optimized for expression of CuZnSOD.

TABLE 3

Comparison of CuZnSOD productivity data in two expression systems in Minimal Medium

| Culture No. | Strain | Promoter | O.D. (660 nm) | DCW (mg/L) | SOD Activity (mg/L) | Specific Productivity (mg active CuZnSOD/mg DCW) | Average Specific Productivity |
|---|---|---|---|---|---|---|---|
| 7 | Sϕ930 | deo | 3.03 | 1151 | 41.0 | 0.036 | 0.039 |
| 8 | pMF-5534 | | 3.15 | 1197 | 50.0 | 0.042 | |
| 9 | MC1655 | osmB | 2.75 | 1045 | 67.0 | 0.064 | 0.060 |
| 10 | pMFO-551 | | 2.80 | 1064 | 61.0 | 0.057 | |

The specific productivity of CuZnSOD expressed under control of the osmB promoter is on the average 1.5 fold higher than that expressed under control of the deo promoter.

Using the expression plasmids harboring the modified osmB promoter of the subject invention, the production of CuZnSOD was scaled up, using methods known in the art, to produce similar high level expression in 500 liter fermentors.

Example 5: Construction of osmB Expression Plasmid for Expression of Human Acetylcholinesterase (AChE)

The human acetylcholinesterase (AChE) gene was isolated and placed under control of the osmB promoter, as shown in FIG. 5. The resulting plasmid designated pMFOA-18 (ATCC Accession No. 69340) contained the AChE gene under control of the osmB promoter and deo ribosomal binding site. Plasmid pMFOA-18 was introduced into E. coli hosts MC1061 (ATCC Accession No. 67364), MC1655

(ATCC Accession No. 69339), W3110 (ATCC Accession No. 67705) and MG294 (*E. coli* Genetic Stock Center, Yale University, New Haven, Conn.). Isolated colonies were seeded into LB medium containing M9 salts and 0.1–0.2% glucose. Cultures were grown at 37° C. for 18 hours, harvested and subjected to SDS-PAGE analysis. As in the case of CuZnSOD, expression levels varied depending on the host. MC1061 harboring pMFOA-18 expressed AChE at high levels of about 10–15% of total cell protein, while all other strains expressed AChE at a levels of about 2–5% of total cell protein. Since AChE is extremely hydrophobic the protein accumulated in the form of aggregated material in inclusion bodies. The expression of AChE under control of the osmB promoter exceeded the level of expression obtained with the $\lambda P_L$ promoter under appropriate conditions for each promoter system.

The AChE gene can be removed from this plasmid e.g. by NdeI and HindIII digestion or by other methods known in the art and replaced by a DNA sequence encoding another polypeptide to obtain expression of this other polypeptide under the control of the osmB promoter. Examples of this procedure are the replacement of the AChE gene by an hGH gene as described in Example 6, and the replacement of the AChE gene by a gene encoding preS1 as described in Example 7. Thus, the osmB promoter system described herein may be used to express a wide variety of polypeptides.

Example 6: Construction of an osmB Expression Plasmid for Expression of Human Growth Hormone a. Introduction of a NdeI Site at the N-terminal Sequence of the Mature hGH In order to introduce an initiation codon, ATG, and an unique restriction site, NdeI (CATATG), at the N-terminal amino acid, Phe, of the mature human growth hormone (hGH) protein, site-directed mutagenesis was carried out using the hGH cDNA plasmid pchGH77 (ATCC Accession No. 69359) (FIG. 6):

Two aliquots of DNA of pchGH77 were digested with the following endonucleases:

aliquot A: PvuI + ScaI aliquot B: EcoRV + BglII

The large DNA fragments of each of the above endonuclease digestions were isolated, mixed and annealed in the presence of the following synthetic oligomer (SEQ. ID NO. 6):

E 5'-GGCTCCAAGAGGGC<u>CATATG</u>TTCCCAACATTCCC-3'
           NdeI

The annealing reaction (2.5 minutes at 95° C., 60 minutes at 40° C. and 60 minutes at 4° C.) was followed by DNA polymerase-Klenow reaction in the presence of all four (4) dNTP's and $T_4$ DNA ligase.

The ligation mixture was used to transform *E. coli* MC1061 (ATCC Accession No. 67364) competent cells.

Clones were screened for the mutated NdeI site by in-situ filter hybridization using as a probe the radiolabeled synthetic oligomer E at high stringency hybridization conditions.

Clones positive in hybridization were further analyzed by restriction enzyme digestion (NdeI) and by DNA sequencing. One of these positive clones was designated plasmid phGH/pBR-N1.

b. Construction of an osmB Expression Plasmid for the Expression of hGH

As shown in FIG. 7, the hGH gene was isolated from plasmid phGH/pBR-N1 and placed under control of the osmB promoter. The resulting plasmid designated pMFO/hGH-9 (ATCC Accession No. 69360), contained the hGH gene under control of the osmB promoter and deo ribosomal binding site (FIG. 7).

c. Expression of hGH

Plasmid pMFO/hGH-9 was used to transform *E. coli* MC1061 (ATCC Accession No. 67364), *E. coli* W3110 (ATCC Accession No. 67705) and *E. coli* W2637 (*E. coli* Genetic Stock Center, Yale University, New Haven, Conn.) competent cells.

Cells of *E. coli* strains MC1061, W3110 and W2637 harboring plasmid pMFO/hGH-9 were grown in LB medium at 37° C. to $O.D._{660}=1.0$. Cells were centrifuged, lysed and total bacterial proteins were analyzed by SDS-PAGE electrophoresis. A major hGH protein band that corresponds to a molecular weight of 22 kD was detected upon Coomassie Blue staining. *E. coli* MC1061 and W3110 expressed hGH at levels of at least 20% of total cell protein.

Example 7: Construction of osmB Expression Plasmid for the Expression of PreS1-HBV a. Reconstruction of N-terminal Amino Acids The HBV-PreS1 region was isolated from plasmid pSP-HBV-3 and ligated to synthetic oligomers F and G as described in FIG. 8.

In order to reconstruct the N-terminal amino acids of PreS1 including NdeI adjacent to the initiation codon ATG, this ligation was carried out in the presence of the large DNA fragment EcoRI-NdeI obtained from plasmid pBR322 (ATCC Accession No. 37017) digested with EcoRI, NdeI and AvaI endonucleases. The newly obtained plasmid was designated pBR-HBV-N.

b. Introduction of a Stop Codon pHBV/BASA was constructed as shown in FIG. 9 in order to introduce a translation stop codon.

c. Construction of osmB Expression Plasmid for the Expression of PreS1-HBV

The HBV-PreS1 fragment was isolated and placed under the control of the osmB promoter as shown in FIG. 10. The resulting plasmid designated pMFO/PreS1 (ATCC Accession No. 69358) contained the PreS1 coding region under control of the osmB promoter and the deo ribosomal binding site.

d. Expression of PreS1

Plasmid pMFO/PreS1 was used to transform *E. coli* strain MC1061 competent cells.

*E. coli* MC1061 cells harboring plasmid pMFO/PreS1 were grown in LB medium at 37° C. to $O.D._{660}=1.0$. Cells were then centrifuged, lysed and total bacterial proteins were analyzed by SDS-PAGE electrophoresis. A PreS1 protein band corresponding to a molecular weight of 14 kD was detected upon Coomassie Blue staining.

REFERENCES

1. Jung, J. U. et al., J. Bacteriol., 171:511–520 (1989).
2. Jung, J. U. et al. J. Biol. Chem., 265:10574–10581 (1990).
3. Hartman, Y. et al. PNAS (USA) 83, 7142–7146, (1986).
4. Fischer, M. et al. App. Microbiol. Biotechnol. 33, 424–428, (1990).
5. Hartman et al., U.S. Pat. No. 4,742,004.
6. Fischer Meir, U.S. Pat. No. 5,248,604.
7. PCT Patent Application No. 92/06106, published as WO 93/10830 on Feb. 4, 1993.

What is claimed is:

1. A method for producing a recombinant eucaryotic polypeptide by use of a plasmid comprising an *E. coli* osmB promoter and DNA encoding the recombinant eucaryotic polypeptide, which method comprises culturing a microorganism transformed by the plasmid under conditions permitting expression of the recombinant polypeptide and recovering the recombinant polypeptide so produced, wherein the polypeptide is selected from the group consisting of human copper-zinc superoxide dismutase, acetylcholinesterase, human growth hormone and pre-S1 hepatitis antigen.

2. A plasmid which upon introduction into a suitable host cell renders the host capable of effecting expression of DNA encoding a desired eucaryotic polypeptide, and thereby effecting production of the polypeptide, the plasmid comprising in 5' to 3' order the following:

a) DNA which includes an *E. coli* osmB promoter region;

b) DNA which includes a ribosomal binding site for rendering mRNA transcribed from the DNA encoding the polypeptide capable of binding to ribosomes within the host cell;

c) an ATG initiation codon; and d) DNA encoding the eucaryotic polypeptide in phase with the ATG initiation codon;

and which additionally includes a DNA sequence comprising an origin of replication from a bacterial plasmid capable of autonomous replication in the host cell and a DNA sequence which contains a gene associated with a selectable or identifiable trait which is manifested when the plasmid is present in the host cell,
wherein the polypeptide is selected from the group consisting of human copper-zinc superoxide dismutase (CuZnSOD), acetylcholinesterase (AchE), human growth hormone (hGH) and pre-S1 hepatitis antigen.

3. The plasmid of claim 2 wherein the *E. coli* osmB promoter region is that depicted in FIG. 2.

4. The plasmid according to claim 2 or 3 wherein the ribosomal binding site is the osmB ribosomal binding site.

5. The plasmid according to claim 2 or 3 wherein the ribosomal binding site is the *E. coli* deo ribosomal binding site.

6. The plasmid according to claim 2 wherein the host cell is a bacterial cell.

7. The plasmid according to claim 6 wherein the bacterial cell is an *E. coli* cell.

8. The plasmid according to claim 2 for the production of human copper zinc superoxide dismutase designated pMFO-551 deposited under ATCC Accession No. 69339.

9. The plasmid according to claim 2 for the production of human acetylcholinesterase designated pMFOA-18 deposited under ATCC Accession No. 69340.

10. The plasmid according to claim 2 for the production of human growth hormone designated pMFO/hGH-9 deposited under ATCC Accession No. 69360.

11. The plasmid according to claim 2 for the production of PreS1 hepatitis antigen designated pMFO-PreS1 deposited under ATCC Accession No. 69358.

12. A host plasmid system for the production of a recombinant eucaryotic polypeptide comprising the plasmid according to claim 2 or 3 in a suitable host cell.

13. The host plasmid system according to claim 12 wherein the host cell is a bacterial host cell.

14. The host plasmid system according to claim 13 wherein the bacterial host cell is *E. coli*.

15. The host plasmid system according to claim 14 wherein the *E. coli* host cell is *E. coli* strain MC1655 or *E. coli* strain MC1061.

16. A host plasmid system for the production of human copper zinc superoxide dismutase comprising the plasmid according to claim 2, wherein the polypeptide is human copper zinc superoxide dismutase, in a suitable host cell.

17. A method for producing CuZnSOD which comprises growing the host plasmid system according to claim 16 under conditions permitting production of the CuZnSOD and recovering the CuZnSOD.

18. A host plasmid system for the production of human acetylcholinesterase comprising the plasmid according to claim 2, wherein the polypeptide is human acetylcholinesterase, in a suitable host cell.

19. A method for producing AChE which comprises growing the host plasmid system according to claim 18 under conditions permitting production of the AChE and recovering the AChE.

20. A host plasmid system for the production of human growth hormone comprising the plasmid according to claim 2, where in the polypeptide is human growth hormone, in a suitable host cell.

21. A method for producing hGH which comprises growing the host plasmid system of claim 20 under conditions permitting production of the hGH and recovering the hGH.

22. A host plasmid system for the production of PreS1 hepatitis antigen comprising the plasmid according to claim 2, wherein the polypeptide is PreS1 hepatitis antigen, in a suitable host cell.

23. A method for producing PreS1 hepatitis antigen which comprises growing the host plasmid system of claim 22 under conditions permitting production of the PreS1 hepatitis antigen and recovering the PreS1 hepatitis antigen.

* * * * *